(12) United States Patent
McKenna et al.

(10) Patent No.: US 6,220,858 B1
(45) Date of Patent: Apr. 24, 2001

(54) APPARATUS FOR PLACEMENT OF DENTAL FILLINGS

(75) Inventors: Mark H. McKenna; Anthony M. Hague, both of Canmore (CA)

(73) Assignee: Mercor Dental Products Inc., Calgary (CA)

( * ) Notice: Subject to any disclaimer, the term of this patent is extended or adjusted under 35 U.S.C. 154(b) by 0 days.

(21) Appl. No.: 09/341,192

(22) PCT Filed: Nov. 25, 1998

(86) PCT No.: PCT/CA98/01091

§ 371 Date: Jul. 6, 1999

§ 102(e) Date: Jul. 6, 1999

(87) PCT Pub. No.: WO99/27866

PCT Pub. Date: Jun. 10, 1999

Related U.S. Application Data (63) Continuation-in-part of application No. 09/026,817, filed on Feb. 20, 1998, now abandoned.

(30) Foreign Application Priority Data

Dec. 2, 1997 (CA) .................................................. 2223359

(51) Int. Cl.[7] ................. A61C 5/04; A61C 5/12; A61C 7/00
(52) U.S. Cl. ............................ 433/39; 433/139; 433/149
(58) Field of Search .............................. 433/39 OR, 40, 433/138, 139, 149

(56) References Cited

U.S. PATENT DOCUMENTS

| | | | |
|---|---|---|---|
| 354,391 | * 12/1886 | Carpenter | 433/139 |
| 1,806,718 | * 5/1931 | Spanier | 433/149 |
| 4,571,188 | 2/1986 | Hamilton | 433/226 |
| 4,578,035 | 3/1986 | Pruitt | 433/149 |
| 4,631,030 | 12/1986 | von Weissenfluh | 433/149 |
| 4,704,087 | 11/1987 | Dragan | 433/39 |
| 4,773,857 | * 9/1988 | Herrin | 433/138 |
| 5,114,341 | * 5/1992 | Kassel | 433/39 |
| 5,316,473 | 5/1994 | Hare | 433/29 |
| 5,380,198 | 1/1995 | Suhonen | 433/39 |
| 5,421,725 | 6/1995 | von Weissenfluh | 433/149 |
| 5,501,595 | * 3/1996 | Brorson | 433/39 |
| 5,505,618 | 4/1996 | Summer | 433/148 |
| 5,607,302 | 3/1997 | Garrison et al. | 433/39 |
| 5,626,476 | 5/1997 | Champagne | 433/226 |
| 5,788,487 | * 8/1998 | Meyer | 433/39 |

FOREIGN PATENT DOCUMENTS

| | | |
|---|---|---|
| 669514 | 3/1989 | (CH) . |
| 4444305 | 12/1994 | (DE) . |
| 0169803 | * 1/1986 | (EP) . |
| 0470552 | * 12/1992 | (EP) . |
| 0594535 | * 4/1994 | (EP) . |
| 0674884 | * 10/1995 | (EP) . |

OTHER PUBLICATIONS

Palodent (Darway) Section Matrix Bands & Bitine Rings.

* cited by examiner

*Primary Examiner*—John J. Wilson
(74) *Attorney, Agent, or Firm*—Bennett Jones LLP (57) ABSTRACT

An apparatus is described for placement of light curable dental fillings. The apparatus includes a matrix formed of light transparent material and shaped to conform to the natural contour of a tooth in the interproximal zone. The matrix is thinned in its central regions to permit a filling to be made which has close contact with an adjacent tooth. A light transparent wedge has also been invented which selectively conducts light to the base of the tooth preparation and which can be used to conduct light interproximally which light has been applied at either end of the wedge. A clamp has been invented for use with the wedge and/or matrix or for use independently of these devices. The clamp is formed to fit over the top portion of the wedge to enhance engagement against the tooth over previous clamps which are prevented from extending over the tooth by engagement against the top of the wedge.

23 Claims, 5 Drawing Sheets

APPARATUS FOR PLACEMENT OF DENTAL FILLINGS

RELATED APPLICATIONS

The present application is a continuation-in-part of U.S. Ser. No. 09/026,817, filed Feb. 20. 1998 (now abandoned).

FIELD OF THE INVENTION

The present invention is directed to an apparatus for placement of fillings and, in particular, an apparatus for placement of light curable dental fillings.

BACKGROUND OF THE INVENTION

Over the past two decades, the dental profession has been urged to provide its clients with natural looking fillings for posterior teeth. Composite resins have been used to provide these natural looking fillings. Composite resins, when cured, have a natural tooth colour, can be placed in one appointment and are free of the toxin mercury.

Before placement, composite resins have a soft putty-like consistency and are generally non-compactable. Fillings formed of composite resin are cured by application of a concentrated source of light. To place a composite resin filling, a matrix is used. A matrix is a device which wraps around a prepared tooth area. It acts as a mold and limits the spread of filling materials beyond desired borders. This mold conforms ideally to the original anatomy of the interproximal tooth structure. Matrices are generally formed from stainless steel or plastic and can be circumferential or sectional. Circumferential matrices fit around the entire circumference of the tooth whereas sectional matrices fit only in one interproximal area of the tooth. Matrices are secured in place by use of wedges and/or clamps. Wedges are triangular in cross section and taper along their length. They are placed between the matrix and the adjacent tooth in order to seal the matrix against the base of the prepared tooth structure. Wedges are generally made of wood or plastic.

The placement of composite resin fillings in the interproximal area has been found to be very problematic. Since the resin is non-compactable, it is very difficult to create a firm contact point between the newly placed filling and the adjacent tooth. The contact point is the point at which the crown of one tooth contacts, or nearly contacts, the crown of an adjacent tooth. If a gap is formed at the contact point, food becomes trapped between the teeth causing gum irritation or inflammation, tooth movement and general patient dissatisfaction. When the curing light source is applied from the direction of the biting surface, this causes the resin material to be drawn away from the base of the proximal tooth preparation and towards the light. When this occurs, the seal of the composite resin at the tooth/filling margin is compromised and microscopic leakage of bacteria and saliva between the tooth and the filling material can occur. This causes sensitivity at the area of the filling and tooth decay often occurs.

The prior art has attempted to overcome these problems by provision of wedges and matrices formed of materials, such as acrylic or thermoplastic, which are transparent to the curing light for resin material used in dental fillings. These devices allow curing light to be conducted interproximally such that curing takes place between the teeth first.

The prior art transparent wedges tend to experience internal reflection of light directed therethough and, thus, have limited usefulness.

SUMMARY OF THE INVENTION

An apparatus has been invented for placement of light curable dental fillings. The apparatus includes a matrix formed of light transparent material and shaped to conform to the natural contour of a tooth in the interproximal zone. A light transparent wedge has also been invented which selectively conducts light to the base of the tooth preparation and which can be used to conduct light interproximally applied from either side of the interproximal zone.

In accordance with a broad aspect of the present invention, there is provided a dental matrix for insertion interproximally between two teeth, the matrix comprising a sheet of material transparent to the light for curing resin dental filling material, the sheet having a first side and a second side and having a selected thickness between the first side and the second side such that it can withstand the forces of being inserted interproximally and having a gum contacting edge and further having a thinned portion positioned thereon and spaced a selected distance from the gum contacting edge, the thickness of the sheet around the thinned portion being greater than the thickness of the material in the thinned portion.

A matrix according to the present invention is of a suitable thickness to be inserted interproximally between two teeth without failing, while providing close spacing at the contact area between adjacent teeth. The matrix is formed in any suitable way to have a thinned portion positioned thereon. In particular, the thinned portion is positioned on the matrix and a thicker portion extends substantially about the thinned portion. The thicker portion acts as a more durable frame for the thinner portion. In one embodiment, the matrix is formed such that its thickness tapers from the edges towards a selected point on the matrix. Alternately, a thinned area having defined edges can be formed at a selected position on the matrix. The matrix acts as a mold against which the composite resin material is pushed. The final cured filling takes the form of the matrix and a raised portion is formed on the filling corresponding to the position of the thinned portion on the matrix. Thus, where the thinned area has defined edges, the edges should be formed to graduate smoothly between the thicker region and the thinned portion such that when the filling is cured it will not have a raised portion that creates dental problems (i.e. catches dental floss). To facilitate manufacture, the matrix is formed as one part, for example, as by molding a sheet of material with a thinner portion therein. Preferably, the sheet around the thinned portion is formed to have a thickness of between about 0.05 to 0.15 mm and the thinned portion is selected to have a thickness of between about 0.03 to 0.07 mm.

The thinned portion is positioned on the matrix such that it is adjacent at the contact area between the teeth when the matrix is positioned between two teeth. Generally, the thinned portion is spaced from the gum contacting edge of the matrix with consideration as to the spacing from the gum to the contact point on an average tooth. The area of the thinned portion can be enlarged to provide for some variation in the spacing from gum to contact point in a tooth. Preferably, the gum contacting edge of the matrix is shaped to conform to the shape of the interproximal gingival margin. In particular, the edge of the matrix which is selected to be positioned against the gum is curved inwardly. Preferably, the matrix is curved such that it is generally concave to allow it to curve around the sides of the tooth and into the tooth neck, when the matrix is positioned against a tooth. The thinned portion is formed in the matrix such that an indentation is positioned on the concave side of the matrix.

The matrix of the present invention is useful with any matrix securing means. In one embodiment, the side edges of the matrix have applied thereto an adhesive material for securing the edges of the matrix to the tooth surface about which it is to be used. The adhesive is selected to be releasable from a tooth surface by application of a selected amount of force.

Other matrix securing means can be used with or without the adhesive such as, for example, wedges and/or clamps. A particularly useful wedge is, of course, also light transparent.

A light transparent wedge has been invented which enhances light transmission interproximally. Thus, in accordance with another broad aspect of the present invention, there is provided a dental wedge formed of materials transparent to the curing light for resin dental filling material, comprising: an elongate body tapering from its first end to its opposite end and being generally triangular in cross section having three sides and the first end having a convex curvature.

The convex curvature causes the first end to act as a lens. This causes light directed at the wedge to be directed through a selected focal point within the wedge and toward the sides of the wedge. The curvature is selected such that light which enters the wedge through the first end is directed toward the sides of the wedge at the portion of the wedge which is intended to be positioned interproximally during use. This position is generally mid way between the ends of the wedge. Preferably, the convex end of the wedge is enlarged over the cross sectional area of the interproximal portion of the wedge to permit more light to be refracted into the wedge. The form of the first end increases the amount of light which enters the wedge over a wedge which has an end with an area equal to the area of the wedge between the three sides. This, in turn, increases the amount of light which impinges on the sides of the wedge to be refracted laterally outwardly from the wedge. Preferably, however, a selected portion of the wedge, which is intended to be the bottom of the wedge, is flattened or otherwise formed so that it does not interfere with the gum during insertion.

The end of the wedge opposite the convex end is preferably flattened such that the wedge has a blunt end. A wedge having such a blunt end provides that light directed at that end will be conducted into the wedge. Thus, light can be applied to either end of the wedge for curing the filling interproximally. Preferably, the blunt end has a slight slant to provide a single leading edge which facilitates insertion between two teeth.

The wedge preferably has on at least one of its sides a portion between its convex end and its blunt end wherein the wedge surface is roughened to refract and/or reflect substantially laterally outwardly light which impinges against the roughened side of the wedge. Preferably, the surface roughening is done over the portion of the wedge through which light is desired to be selectively directed. For example, in one embodiment the surface of the wedge is roughened on at least one side in a region generally central between the first end and the opposite end and along one edge.

The surface roughening can be completed in any suitable way. For example, the roughening can be by treating the surface of the wedge (i.e. by scratching) or by formation during molding (i.e. by the formation of striations on the mold or by a roughening finish such as electrical discharge machining). Where striations are used, they are formed on the wedge to extend perpendicular to the long axis of the wedge. Preferably, each striation has a first angular face and a second angular face which converge at the bottom of the striation. The angular faces of the striations are selected to have an angle relative to the end of the wedge such that light impinging thereon will be refracted outwardly or will be refracted toward the opposite angular face of the striation to reflect outwardly therefrom. This angle will be selected with consideration to characteristics, such as the refractive index of the material of the wedge and the curvature of the end of the wedge, if any. In one embodiment, the striations are each formed with first and second angular faces which extend at an angle of between about 30° to 60° relative to the plane of the sides or stated another way relative to the long axis of the wedge, and preferably 45° relative to the plane of the side or the long axis of the wedge. Preferably, the wedge is curved along its length to conform to the interproximal tooth contours.

The wedge is particularly useful for holding a matrix in place and for conducting curing light interproximally. The wedge can be used with a clamp which is formed to fit together with the wedge and uses the wedge to ensure proper positioning and engagement of the clamp. Thus, in accordance with another broad aspect of the present invention, there is provided a dental retainer clamp for clamping simultaneously over a dental matrix and a dental wedge comprising a pair of arms extending in a plane each arm having a tine depending therefrom, each tine having a distal end extending out from the plane of the arms, the distal end being bifurcated into two extensions which define therebetween a notch on the distal end sized to fit over a portion of a dental wedge.

The arms are held under tension and require a force to be applied to move them apart. Each tooth engaging surface is defined by a tine extending out from the plane of the arms. The tine is sized to extend over at least a portion of the tooth about which the clamp is engaged. The outer end of each tine is bifurcated into two extensions. Between the extensions is formed a notch formed for fitting over a portion of the wedge. The notch is preferably formed to closely follow the contour of the upper portion of the wedge and the extensions extend down along the sides of the wedge. A clamp without a notch formed therein could only be pushed down over the tooth until it abutted against the wedge. Such a wedge has a tendency to "pop off" the tooth over which it is clamped. However, the extensions of the present clamp provide that the clamp can be pushed down further over the tooth and a greater amount of clamp surface area can be in contact with the tooth. This increases engagement of the clamp over the tooth and reduces the tendency of the clamp from "popping off" the tooth.

In one embodiment, where it is desired that the clamp block light from moving therepast and interproximally, the extensions are formed of a material to block light. Using such a clamp, light is prevented from passing interproximally except through the wedge.

In another embodiment, the extensions are formed of a light transmitting material. The light transmitting material is preferably bonded to the arms of the clamp. A clamp with light transparent extensions permits light to pass interproximally both through the wedge and through the clamp.

In accordance with another broad aspect of the present invention, there is provided a dental matrix retainer assembly comprising: a dental wedge formed of materials transparent to the curing light for resin dental filling material, including an elongate body tapering from its first end to its opposite end and being generally triangular in cross section having three sides, the first end having a convex curvature such that light directed at the first end will be refracted toward the sides of the wedge between the first end and the opposite end; and a clamp having a pair of arms extending in a plane each arm having a tine attached thereto, each tine having a distal end extending out from the plane of the arms and having a notch on the distal end sized to fit over a portion of a dental wedge.

In accordance with another broad aspect of the present invention, there is provided a method for conducting a dental restoration on a tooth, the method comprising: removing a portion of the tooth to form a cavity; applying a matrix against the tooth to act as a mold for resin dental filling material, the matrix being a sheet of material transparent to the light for curing the resin dental filling material, the sheet having a first side and a second side and having a selected thickness between the first side and the second side such that it can withstand the forces imparted by interproximal insertion, the sheet further having a gum contacting edge and a thinned portion positioned thereon to define an indentation in the surface of the sheet, the thinned portion spaced a selected distance from the gum contacting edge, the thickness of the sheet around the thinned portion being greater than the thickness of the material in the thinned portion; inserting a dental wedge between the matrix and the adjacent tooth, the dental wedge being formed to conduct light therethrough; clamping a dental clamp over the matrix; introducing an amount of the resin dental filling material to the cavity and against the matrix; applying an amount of curing light to the resin dental filling material through the wedge to cure the resin dental filling material.

BRIEF DESCRIPTION OF THE DRAWINGS

A further, detailed, description of the invention, briefly described above, will follow by reference to the following drawings of specific embodiments of the invention. These drawings depict only typical embodiments of the invention and are therefore not to be considered limiting of its scope. In the drawings.

DETAILED DESCRIPTION OF THE PRESENT INVENTION

Figure 1A:
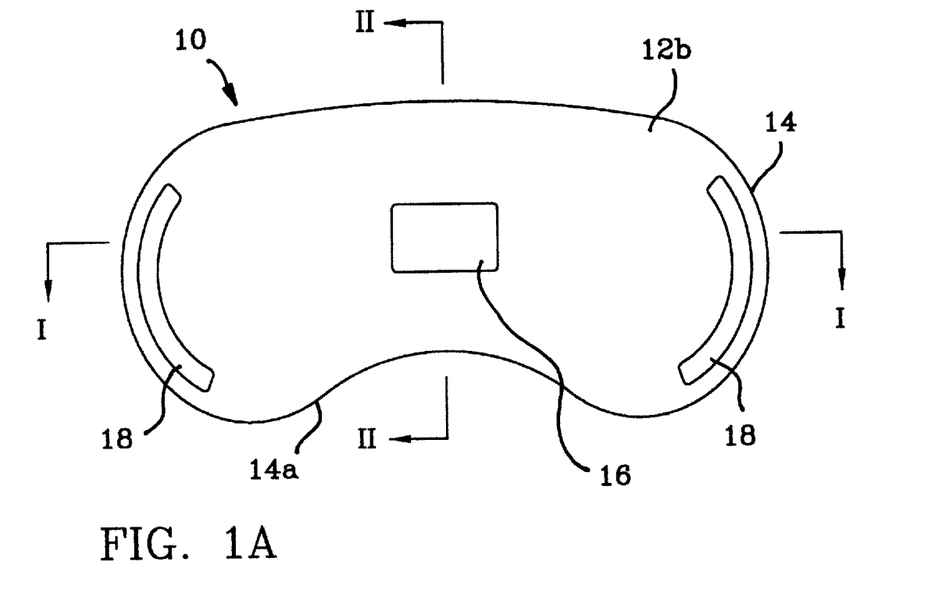
FIG. 1A is a side plan view of a dental matrix according to the present invention.
Figure 1B:
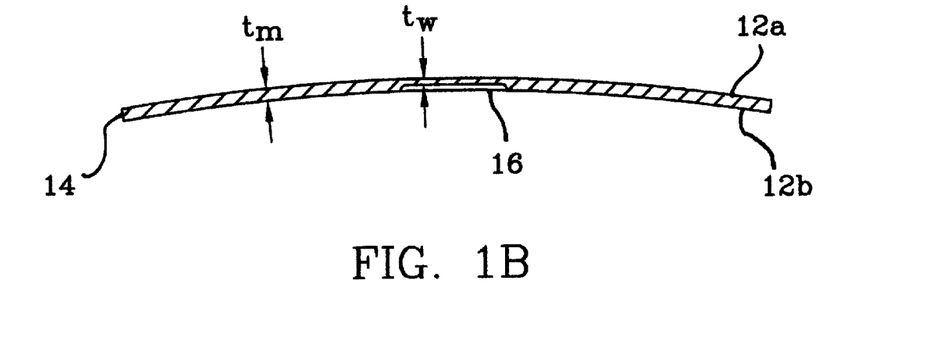
FIG. 1B is a sectional view along line 1—1 of FIG. 1A.
Figure 1C:
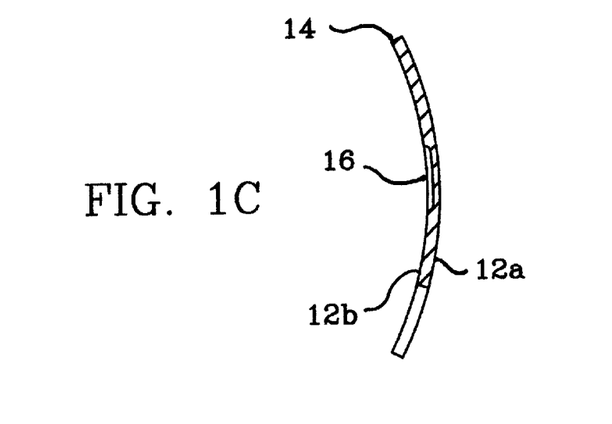
FIG. 1C is a sectional view along line 11—11 of FIG. 1A.

Referring to FIGS. 1A to 1C, there is shown a matrix 10 according to the present invention. Matrix 10 is formed of material, such as acrylic or thermoplastic which is transparent to the light used in curing composite resin dental fillings and includes two sides 12a, 12b and a contoured edge 14. Side 12b is the side of the matrix which will be adjacent the prepared tooth and against which the resin will be placed. Side 12b will hereinafter be referred to as the resin contacting side. Matrix 10 is preformed such that an edge 14a is shaped to conform to the contour of the interproximal gingival margin. In particular, edge 14a which contacts the gum is curved inwardly toward the centre of the matrix.

Matrix 10 has formed therein a portion 16 of reduced thickness $t_w$ when compared to the thickness $t_m$ of the remainder of the matrix, such that an indentation is formed on the resin contacting side 12b of the matrix. The outer portion of the matrix is selected to be of thickness which is suitable for insertion interproximally and which provides sufficient rigidity to permit such insertion substantially without damage thereto. In particular, the portion of matrix 10 around thinned portion 16 has a thickness $t_m$ of between about 0.05 to 0.15 mm and, preferably, 0.1 mm. Portion 16 is selected to be thinner to permit the filling material to be introduced into the indentation so that when the filling is cured an extended portion will be formed at the contact area of the filling and only a small space will be left between adjacent teeth. This prevents an unhealthy and uncomfortable space from being formed between adjacent teeth. The thickness of the thinned portion is preferably selected to be as thin as possible, with consideration as to the properties of the material of the matrix, to prevent damage thereto by resin being applied thereagainst. In particular, thinned portion 16 is preferably selected to have a thickness $t_w$ of between about 0.03 to 0.07 mm and, most preferably, 0.05 mm. To ensure that portion 16 is correctly positioned when inserted for use, portion 16 is spaced from gum contacting edge 14a a distance which corresponds to the distance between the gum and the contact point in an average tooth. In particular, the thinned portion is preferably spaced between about 1.0 and 5.0 mm from edge 14a. Preferably, the area of the thinned portion is enlarged to allow for some variation in the distance from the gum to the contact point. A preferred thinned portion has a height of between 2 to 4 mm and a width of about 2 to 4 mm. Matrices according to the present invention can be produced in various sizes to, for example, correspond to child or adult teeth, an adult's tooth generally having a greater distance between the gum and the contact point than a child's tooth.

While the thinned portion has been shown as a rectangle, it is to be understood that it can take other forms such as a circle or an ellipse. In addition, it is to be understood that the thinned portion can have defined, smoothly rounded graduated sides, as shown, or can be formed by tapering the thickness of the matrix more gradually.

Matrix 10 is preferably curved to be generally concave (FIGS. 1B, 1C) and the indentation resulting from the thinned portion is positioned on the concave side. This curvature permits the matrix to follow the side and neck curvature of a tooth beside which it has been inserted. Adhesive 18 can be applied to side edges of the matrix to permit attachment about the tooth against which it is to be used. Adhesive is suitable for attaching the matrix to a tooth surface but is releasable to permit pulling or peeling matrix from the tooth surface, when desired.

Referring to FIGS. 2A to 2D, a wedge 20 according to the present invention is shown. Wedge 20 is tapered along its length from its first end 22 to its second end 24. Wedge 20 is formed to have three side surfaces 26a, 26b, 26c and is, therefore, triangular in cross section. The cross sectional area of the wedge between sides 26a, 26b, 26c is selected such that the wedge can fit between two teeth. Preferably, side surfaces 26a to 26c are slightly concave to facilitate insertion between teeth. The wedge is preferably curved along its length to conform to the curvature of the teeth in the interproximal area.

The wedge is formed of material which is transparent to the light used for curing resin dental fillings and is formed to enhance light transmission to the interproximal zone over prior art wedges. In particular, first end 22 of wedge 20 is formed as a lens with a convex curvature such that light passing into wedge through end 22 is refracted through a focal point 38 and toward the sides of the wedge. End 22 is enlarged over the cross sectional area between sides 26a, 26b, 26c. Where desired, a lower side of end 22 can be rounded or flattened to avoid aggravating a patient's gum during use.

Figure 2A:
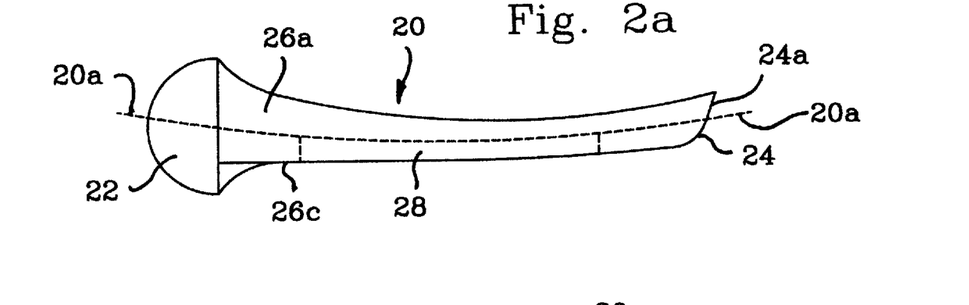
FIG. 2A is a side elevation view of a wedge according to the present invention.
Figures 2B, 2C:
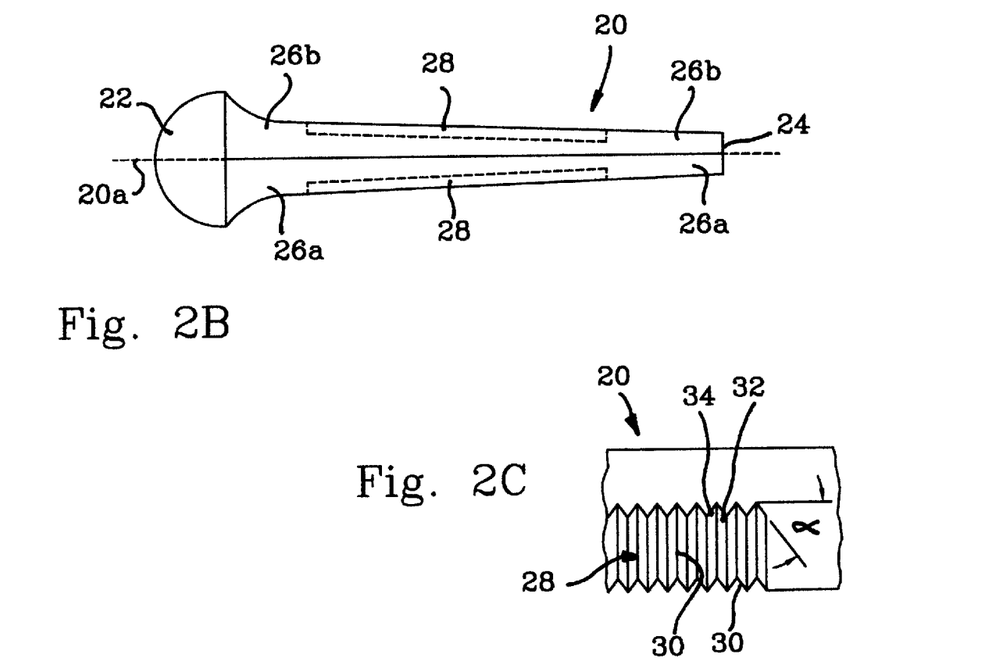
FIG. 2B is a top plan view of the wedge of FIG. 2A.
FIG. 2C is a side elevation view of a portion along the length of a wedge according to the present invention showing detail of the striations.

Along a portion of each of two sides 26a, 26b is formed a striated region 28. Each striated region 28 includes a plurality of striations 30 selected to refract and reflect light impinging thereon laterally outwardly from the wedge. The striations 30 each have a first angular face 32 and a second angular face 34 and extend perpendicular to the center line 20a of the wedge between ends 22, 24. The angular faces 32, 34 are selected to slope into the wedge at an angle selected to permit light being conducted through the wedge to refract outwardly when it impinges on the angular face. The angle at which the angular faces slope inwardly relative to the plane of the side is selected with consideration as to the angle at which light will be impinging on the faces, as determined by the curvature of end 22, and the refractive index of the wedge material. Generally, the angular faces are preferably selected to slope at an angle of between about 30° and 60°, and most preferably about 45°, relative to the plane defined by the side on which the striation is formed.

Figure 2D:
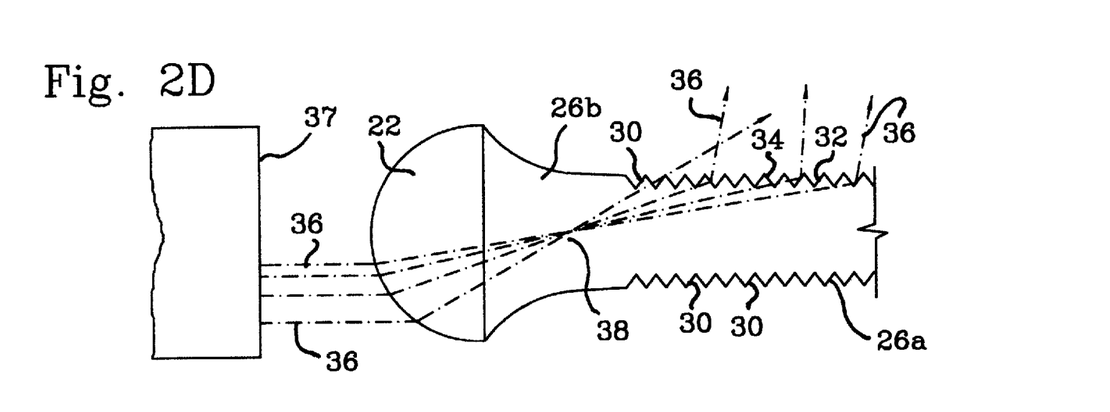
FIG. 2D is top plan view of the wedge having a source of concentrated light directed at an end thereof.

End 22 and striated regions 28 cooperate to enhance light transmission to the interproximal zone. Referring particularly to FIG. 2D, when light energy, indicated by phantom lines 36, is directed from a source 37 toward end 22, the light is refracted through a focal point 38 and beyond that point to the sides 26a, 26b of the wedge. The curvature of end 22 is selected such that the refracted light will impinge on the sides of the wedge at a position between end 22 and end 24. When the light impinges on striated regions 28, the light will be refracted through face 34. This light will then pass directly laterally outwardly from wedge or will be reflected off side 32 laterally outwardly from the wedge. As would be understood, the curvature of end 22 must be selected such that the focal point is positioned within the wedge and the light is directed at a useful position along the sides of the wedge.

While all of the sides of the wedge can be striated, preferably only a selected region of one or more selected sides has formed thereon a striated region so that light is refracted laterally outwardly selectively through this region. In particular, preferably as shown in FIG. 2B, the striated region extends centrally between the ends of the wedge so that light is concentrated in the interproximal zone. Preferably, the striated region extends from a central position along the width of a side out toward one of the edges. The positioning of the striated region in this way provides that when the wedge is positioned interproximally for use, the striated region will be selectively positioned adjacent the margin 38 (FIG. 4A) between the filling and the tooth. Thus, light refracting from the wedge will be directed laterally outwardly selectively toward margin 38.

End 24 is formed to be blunt such that light directed from outside the wedge toward end 24 will be conducted into and through the wedge, rather than being reflected. Preferably, end 24 is slanted to have a leading edge 24a which facilitates insertion of wedge 20 between teeth. End 24 can be narrowed, as desired, to facilitate entry between teeth.

The striations can be replaced by other forms of surface roughening and this surface roughening can be applied to various surfaces of the wedge. As an example, striations can be replaced with roughening applied to sides 26a and 26b, while the remainder of the surfaces of the wedge, including end 22, and side 26c, are smoothly finished. In one embodiment, not shown, roughening is accomplished by electrical machining discharge (EDM) finishing of the mold surfaces for the wedge. This creates a surface of random peaks and valleys on the wedge outer surface. Roughening is selected to be a degree suitable for refracting light outwardly from within the wedge.

Figure 3A:
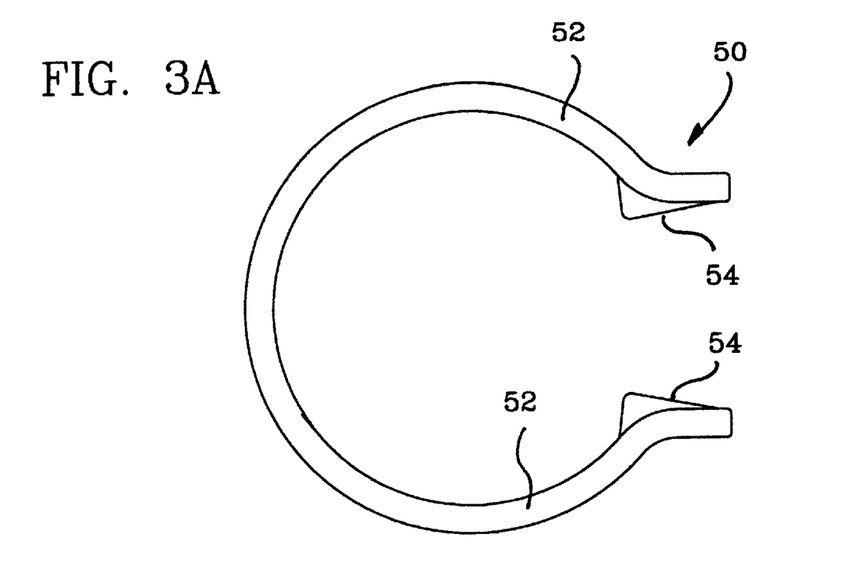
FIG. 3A is a top plan view of a clamp according to the present invention.
Figure 3B:
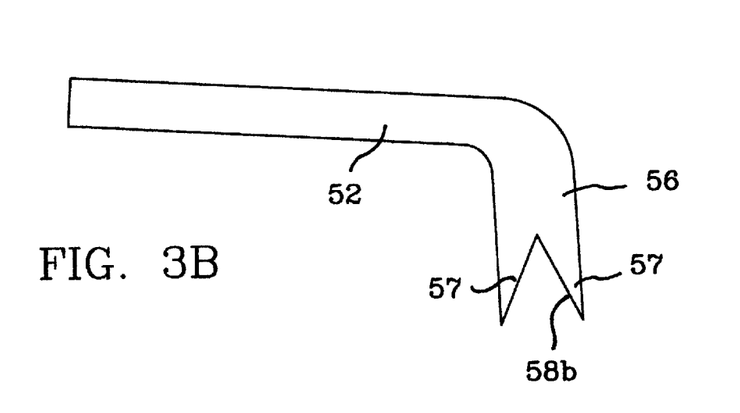
FIGS. 3B and 3C are side elevational views of the clamp of FIG. 3A.
Figure 3C:
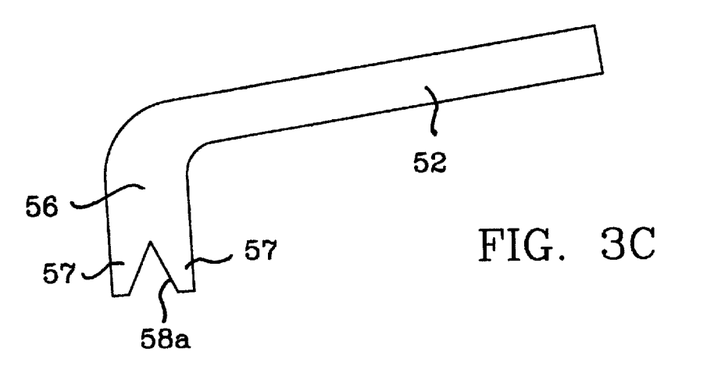

Referring to FIGS. 3A to 3C, a clamp 50 is shown which can be used to maintain simultaneously a matrix and a wedge in position. Clamp 50 is generally semi-circular or U-shaped in plan view (FIG. 3A) and has a pair of arms 52 extending in a plane. Arms 52 are under tension and require that a force be applied to move them apart. Each arm 52 has a tooth engaging surface 54 thereon. Surfaces 54 are defined by a tine 56 depending outwardly from the plane of the arms. Tine 56 is sized to extend over at least a portion of a tooth about which it is engaged. Tine 56 is bifurcated at its end to form two extensions 57. Extensions 57 define therebetween a notch 58a, 58b. Notch is formed to be V-shaped so that it fits over the upper portion of a wedge, such as that wedge shown in Figure a. The positioning of notches 58a, 58b over the wedge ensures proper placement of clamp 50 down over the tooth to prevent it from "popping off". Preferably, as shown, in the illustrated embodiment, the notches 58a, 58b are formed such that notch 58a begins at a point further removed from arm 52 to correspond to the tapering size of the wedge. To facilitate use of such a notched clamp, right and left-hand clamps are provided.

Figure 3D:
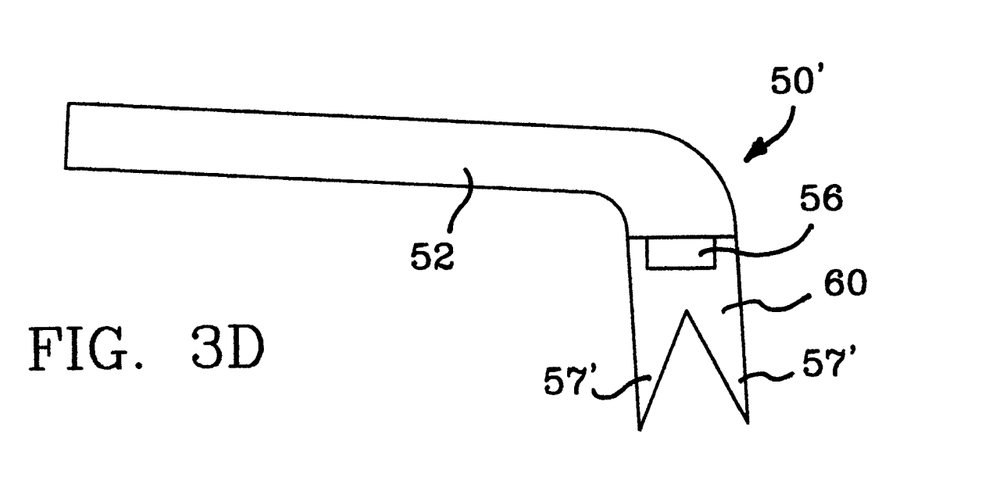
FIG. 3D is a side elevation view of a clamp according to another aspect of the present invention.

Clamp 50 is preferably formed of material, such as stainless steel, which is opaque to the curing light. Thus, when light is directed from the side of a dental preparation, curing light will be shielded by extensions 57 of tine 56 from the upper portion of the dental preparation and will preferentially be directed through the wedge.

Where it is desirable to provide for visual access through the clamp (i.e. for visual inspection to determine if the lateral portions of the cavity are filled properly), a portion of the clamp can be formed of light transparent material. Referring to FIG. 3D, a clamp 50' is shown having extensions 57' formed of light transparent material. Clamp 50' includes arms 52 having short posts 56' extending therefrom. A light transparent portion 60 is bonded to each post 56'. Light transparent portion 60 includes integrally formed extensions 57'.

Figure 4A:
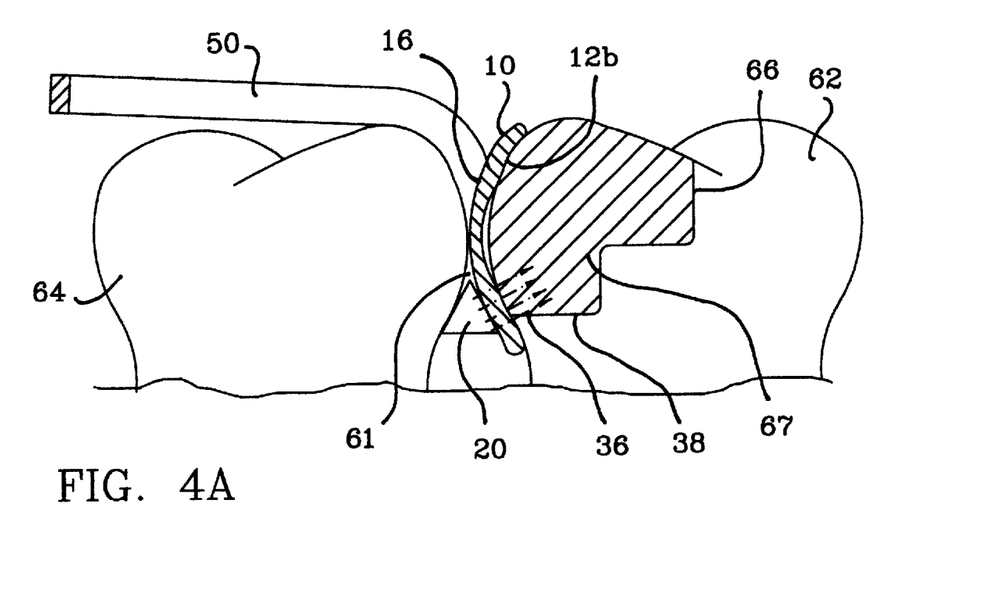
FIG. 4A is a sectional view through two teeth having a matrix band and wedge according to the present invention positioned therebetween for a dental restoration.
Figure 4B:
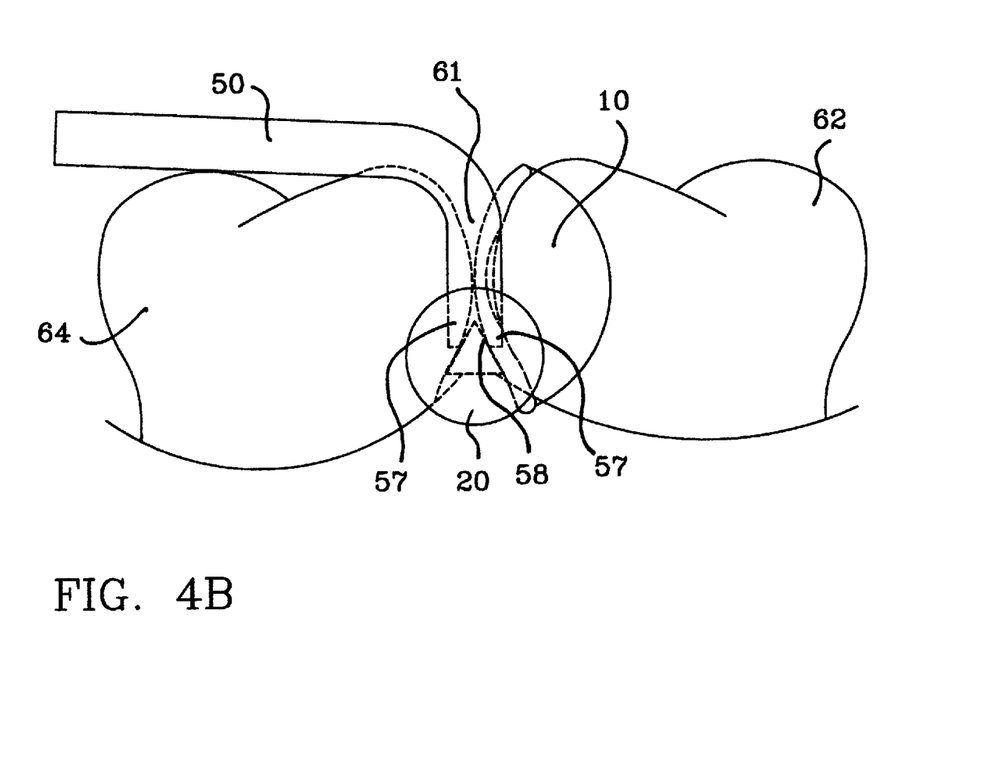
FIG. 4B is a side elevation view of the teeth as in FIG. 4A, except with a clamp also positioned to retain the matrix.

While the matrix 10, wedges 20 or 20' and clamps 50 or 50' can be used independently of each other with other prior art devices, in a preferred embodiment the matrix, wedge and the clamp of the present invention are used together to effect placement of a dental filling which is cost effective and which provides firm contact in the contact area 61 between the placed filling material and the prepared tooth and, thereby, a well sealed margin 38. FIGS. 4A and 4B, schematically illustrate a restoration procedure which is being performed on a tooth 62 using a matrix 10, wedge 20 and clamp 50. Tooth 62 is adjacent a second tooth 64. Tooth 62 has had a portion of its crown removed to form a cavity 66 for accepting an amount of dental filling material 67 such as light curable composite resin.

Between teeth 62, 64 is inserted matrix 10 which acts as a mold around cavity 66 against which the filling material can be placed. Side 12b of matrix is positioned adjacent tooth 62. Wedge 20 is inserted between the teeth to extend into or through the interproximal area. End 22 is exposed for directing theretowards concentrated light. Wedge 20 forces matrix 10 in close contact with tooth 62 and is useful to conduct light interproximally.

To secure the upper portion of matrix 10 against tooth 62, clamp 50 is engaged about tooth 62 and matrix 10. To engage clamp 50 over the tooth and the matrix, a device is used to force the arms 52 of the clamp apart so that extensions 57 of tines 56 can be forced down on either side of the tooth. Tine 56, when placed, contacts both tooth 62 and 64 and shields the interproximal area therebetween. Notches 58 fit over upper portion of wedge 20.

Matrix 10 is thereby securely held against tooth 62 and composite resin 67 can be introduced to cavity 66. To cure the resinous material, concentrated light is directed at end 22 of wedge 10. The light is conducted through the wedge and is refracted and reflected laterally outwardly therefrom by the striations on the wedge. Light is prevented from curing the upper portion of the preparation by the positioning of the extensions 57 of clamp 50 and by the positioning of the striated region on the wedge.

It will be apparent that many other changes may be made to the illustrative embodiments, while falling within the scope of the invention and it is intended that all such changes be covered by the claims appended hereto.

The embodiments of the invention in which an exclusive property or privilege is claimed are defined as follows:

1. A dental wedge formed of materials transparent to the curing light for resin dental filling material, comprising: an elongate body having sides and tapering from its first end to its opposite end, the first end having a convex curvature such that light directed at the first end will be refracted into the wedge and through the wedge toward the sides of the wedge between the first end and the opposite end.

2. The dental wedge of claim 1, the sides of the wedge defining a cross sectional area therebetween and the first end of the wedge being enlarged over the maximum cross sectional area defined between the sides of the wedge.

3. The dental wedge of claim 1 wherein the opposite end of the wedge has a planar face separate from the sides of the wedge.

4. The dental wedge of claim 1 wherein the elongate body comprises an outer surface and at least a portion of the outer surface is roughened to refract light passing through the wedge laterally outwardly from the outer surface of the wedge.

5. The dental wedge of claim 4 wherein the roughened outer surface is formed to have a texture similar to that formed by electrical discharge machining and to refract light passing through the wedge laterally outwardly from the wedge.

6. The dental wedge of claim 4 wherein the roughened outer surface is a surface striation extending perpendicularly between the first end and the opposite end on at least one side thereof, the surface striation formed to refract light passing through the wedge laterally outwardly from the wedge.

7. The dental wedge of claim 6 having a plurality of surface striations extending along at least one side.

8. The dental wedge of claims 6 or 7 wherein each surface striation is formed with a first sloping face and a second sloping face which converge at the bottom of the striation, the first sloping face and the second sloping face extending at an angle of between about 30° to 60° relative to the plane of the side on which they are formed.

9. A dental matrix retainer assembly comprising:
 a dental wedge formed of materials transparent to the curing light for resin dental filling material, including an elongate body having sides and tapering from its first end to its opposite end, the first end having a convex curvature such that light directed at the first end will be refracted into the first end of the wedge and through the wedge toward the sides of the wedge between the first end and the opposite end; and
 a clamp having a pair of arms extending in a plane each arm having a tine attached thereto, each tine having a distal end extending out from the plane of the arms and having a notch on the distal end sized to fit over a portion of a dental wedge.

10. The dental matrix retainer assembly of claim 9 wherein the notches are formed to conform to the shape of the portion of the dental wedge over which it is selected to fit.

11. The dental matrix retainer assembly of claim 9, the sides of the wedge defining a cross sectional area therebetween and the first end of the wedge having a cross section area greater than the maximum cross sectional area defined between the sides of the wedge.

12. The dental matrix retainer assembly of claim 9 wherein the opposite end of the wedge has a planar face separate from the sides of the wedge.

13. The dental matrix retainer assembly of claim 9 wherein the elongate body comprises an outer surface and at least a portion of the outer surface is roughened to refract light passing through the wedge laterally outwardly from the outer surface of the wedge.

14. The dental matrix retainer assembly of claim 13 wherein the roughened outer surface is formed to have a texture similar to that formed by electrical discharge machining and to refract light passing through the wedge laterally outwardly from the wedge.

15. The dental matrix retainer assembly of claim 13 wherein the roughened outer surface is a surface striation extending perpendicularly between the first end and the opposite end on at least one side thereof, the striation formed to refract light passing through the wedge laterally outwardly from the wedge.

16. The dental matrix retainer assembly of claim 15 having a plurality of surface striations extending along at least one side.

17. The dental matrix retainer assembly of claim 15 or 16 wherein each surface striation is formed with a first sloping face and a second sloping face which converge at the bottom of the striation, the first sloping face and the second sloping face extending at an angle of between about 30° to 60° relative to the plane of the side on which they are formed.

18. A dental matrix for insertion interproximally between two teeth, the matrix comprising a sheet of material transparent to the light for curing resin dental filling material, the sheet having a first side and a second side and having a selected thickness between the first side and the second side such that it can withstand the forces imparted by interproximal insertion and one side of the sheet being generally concave, the sheet further having a gum contacting edge and a thinned portion thereon to define an indentation positioned on the concave side of the sheet, the thinned portion spaced a selected distance from the gum contacting edge, the thickness of the sheet around the thinned portion being greater than the thickness of the material in the thinned portion.

19. The dental matrix of claim 18 wherein the thinned portion is spaced from the gum contacting edge of the matrix with consideration as to a known spacing from a gum to a contact point on an average tooth.

20. The dental matrix of claim 18 wherein the gum contacting edge of the sheet is curved inwardly.

21. The dental matrix of claim 18 wherein an adhesive is applied on the concave side of the sheet.

22. A method for conducting a dental restoration on a tooth, the method comprising:

removing a portion of the tooth to form a cavity;

applying a matrix against the tooth to act as a mold for resin dental filling material, the matrix being a sheet of material transparent to the light for curing the resin dental filling material, the sheet having a first side and a second side and having a selected thickness between the first side and the second side such that it can withstand the forces imparted by interproximal insertion and one side of the sheet being generally concave, the sheet further having a gum contacting edge and a thinned portion thereon to define an indentation positioned on the concave side of the sheet, the thinned portion spaced a selected distance from the gum contacting edge, the thickness of the sheet around the thinned portion being greater than the thickness of the material in the thinned portion;

inserting a dental wedge between the matrix and the adjacent tooth, the dental wedge being formed to conduct light therethrough;

clamping a dental clamp over the matrix;

introducing an amount of the resin dental filling material to the cavity and against the matrix; and applying an amount of curing light to the resin dental filling material through the wedge to cure the resin dental filling material.

23. A method for conducting a dental restoration on a tooth, the method comprising:

removing a portion of the tooth to form a cavity;

applying a matrix against the tooth to act as a mold for resin dental filling material, the matrix being a sheet of material transparent to the light for curing the resin dental filling material;

inserting a dental wedge between the matrix and the adjacent tooth, the dental wedge being formed of materials transparent to and able to conduct the curing light for resin dental filling material, the dental wedge including: an elongate body having sides and tapering from its first end to its opposite end, the first end having a convex curvature such that light directed at the first end will be refracted into the wedge and through the wedge toward the sides of the wedge between the first end and the opposite end;

clamping a dental clamp over the matrix;

introducing an amount of the resin dental filling material to the cavity and against the matrix; and applying an amount of curing light to the resin dental filling material through the wedge and matrix to cure the resin dental filling material.

\* \* \* \* \*